United States Patent [19]

Stoltefuss et al.

[11] Patent Number: 5,504,210

[45] Date of Patent: Apr. 2, 1996

[54] 3-QUINOLYL-SUBSTITUTED DIHYDROPYRIDINES AND THEIR USE IN MEDICAMENTS

[75] Inventors: Jürgen Stoltefuss, Haan; Siegfried Goldmann, Wuppertal; Alexander Straub, Wuppertal; Martin Bechem, Wuppertal; Rainer Gross, Wuppertal; Siegbert Hebisch, Bottrop; Joachim Hütter; Howard-Paul Rounding, both of Wuppertal, all of Germany

[73] Assignee: Bayer Aktiengesellschaft, Leverkusen, Germany

[21] Appl. No.: 230,286

[22] Filed: Apr. 20, 1994

[30] Foreign Application Priority Data

Apr. 27, 1993 [DE] Germany .......................... 43 13 692.3

[51] Int. Cl.[6] .......................... C07D 401/04; A61K 31/47

[52] U.S. Cl. .............................................. 546/167; 514/314

[58] Field of Search .............................. 546/167; 514/314

[56] References Cited

U.S. PATENT DOCUMENTS

| | | | |
|---|---|---|---|
| 4,145,432 | 3/1979 | Sato | 424/266 |
| 4,248,873 | 2/1981 | Bossert et al. | 424/256 |
| 5,100,900 | 3/1992 | Stoltefuss et al. | 514/314 |
| 5,204,472 | 4/1993 | Stoltefuss et al. | 546/168 |

*Primary Examiner*—David B. Springer
*Attorney, Agent, or Firm*—Sprung Horn Kramer & Woods

[57] ABSTRACT

The invention relates to new 3-quinolyl-substituted dihydropyridines, processes for their preparation and their use in medicaments, in particular in agents for the treatment of cardiovascular diseases.

8 Claims, No Drawings

3-QUINOLYL-SUBSTITUTED DIHYDROPYRIDINES AND THEIR USE IN MEDICAMENTS

The invention relates to new 3-quinolyl-substituted dihydropyridines, processes for their preparation and their use in medicaments, in particular in agents for the treatment of cardiovascular diseases.

It is already known that 1,4-dihydropyridines have vasodilating properties and can be used as coronary agents and antihypertensives. It is furthermore known that 1,4-dihydropyridines cause inhibition of the contractility of smooth and cardiac muscles and can be employed for the treatment of coronary and vascular diseases.

Furthermore, 4-quniolyl -dihydropyridines having a positively inotropic action are already known from U.S. Pat. No. 5,100,900.

The present invention relates to new 3-quniolyl substituted dihydropyridines of the general formula (I)

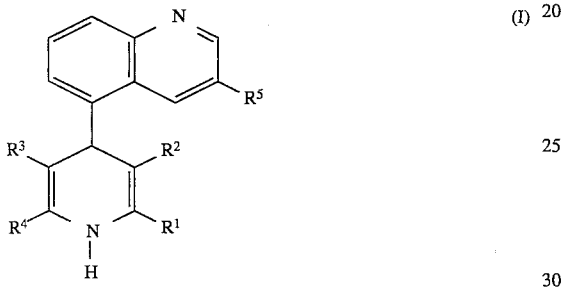

in which $R^1$ and $R^4$ are identical or different and represent hydrogen, amino, cyano, formyl or trifluoromethyl, or represent straight-chain or branched alkyl having up to 8 carbon atoms, which is optionally substituted by hydroxyl or by a group of the formula —$NR^6R^7$, —O—CO—$R^8$, —O—$(CH_2)_a$-$OR^{8'}$ or —O—$(CH_2)_b$—$NR^9R^{10}$, wherein $R^6$, $R^7$, $R^9$ and $R^{10}$ are identical or different and denote hydrogen, phenyl or straight-chain or branched alkyl having up to 6 carbon atoms, $R^8$ and $R^{8'}$ are identical or different and denote straight-chain or branched alkyl having up to 6 carbon atoms, and a and b are identical or different and denote the number 2, 3, 4 or 5, $R^2$ represents a group of the formula —CO—$NR^{11}R^{12}$ or —CO—A—$R^{13}$, wherein $R^{11}$ and $R^{12}$ are identical or different and denote hydrogen or a straight-chain, branched or cyclic, saturated or unsaturated hydrocarbon radical having up to 8 carbon atoms, which is optionally substituted by halogen, hydroxyl or cyano or by aryl, aryloxy or arylthio having in each case 6 to 10 carbon atoms or by a 5- to 7-membered, saturated or unsaturated heterocyclic radical having up to 3 hereto atoms from the series comprising S, N and O, it being possible for the cyclic radicals in turn to be substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denote aryl having 6 to 10 carbon atoms or a 5-to 7-membered, saturated or unsaturated heterocyclic radical having up to 3 hetero atoms from the series comprising S, N and O, which are optionally substituted up to twice in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or $R^{11}$ and $R^{12}$, together and including the nitrogen atom, form a 3- to 8-membered, saturated or unsaturated heterocyclic radical, which can optionally be interrupted by an oxygen atom or by a radical of the formula $S(O)_d$, —CO— or —$NR^{15}$, wherein d denotes the number 0, 1 or 2, $R^{15}$ denotes hydrogen or aryl having 6 to 10 carbon atoms, which is optionally substituted up to twice in an identical or different manner by halogen or cyano or by straight-chain or branched alkyl, alkoxy, alkylthio or alkoxycarbonyl having in each case up to 8 carbon atoms or halogenoalkyl, halogenoalkoxy or halogenoalkylthio having in each case up to 4 carbon atoms, or denotes a cyclic, straight-chain or branched saturated or unsaturated hydrocarbon radical having up to 8 carbon atoms, which is optionally substituted by hydroxyl or halogen or by aryl having 6 to 10 carbon atoms or a 5- to 7-membered, saturated or unsaturated heterocyclic radical having up to 3 hetero atoms from the series comprising S, N and O, it being possible for the cyclic radicals in turn to be substituted up to twice in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and the heterocyclic radical is optionally substituted by straight-chain or branched alkoxy or alkylthio having in each case up to 4 carbon atoms, halogen, aryl having 6 to 10 carbon atoms or a 5- to 7-membered, saturated or unsaturated heterocyclic radical having up to 3 hetero atoms from the series comprising S, N and O or by straight-chain or branched alkyl having up to 4 carbon atoms, which in turn can be substituted by aryl having 6 to 10 carbon atoms, A denotes a direct bond or an oxygen atom, $R^{13}$ denotes hydrogen or aryl having 6 to 10 carbon atoms or a 5- to 7-membered, saturated or unsaturated heterocyclic radical having up to 3 hetero atoms from the series comprising S, N and O, the cyclic radicals optionally being substituted up to 3 times in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or denotes a cyclic, straight-chain or branched, saturated or unsaturated hydrocarbon radical having up to 10 carbon atoms, which is optionally interrupted up to 3 times in an identical or different manner by oxygen or by —CO—, —CO—NH—, —O—CO—, —CO—O—, —NH—CO—, —$SO_2$—NH—, —NH—$SO_2$—, —$S(O)_e$— or —$NH^{16}$—, wherein e has the above-mentioned meaning of d and is identical to or different from this, $R^{16}$ has the above-mentioned meaning of $R^{15}$ and is identical to or different from this, or the hydrocarbon radical is optionally interrupted up to 3 times in an identical or different manner by arylidene having 6 to 10 carbon atoms or heterocyclic radicals of the formulae

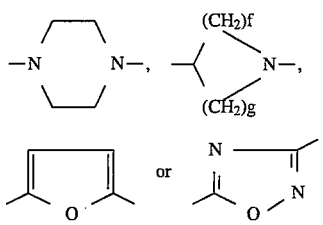

wherein f and g are identical or different and denote the number 1 or 2, and wherein arylidene can be substituted by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, and the hydrocarbon radical is optionally substituted up to 3 times in an identical or different manner by cycloalkyl having 3 to 8 carbon atoms, halogen, nitro, cyano, hydroxyl, $-O-NO_2$, or straight-chain or branched alkylthio, alkoxy or acyloxy having in each case up to 8 carbon atoms or by aryl, aryloxy or arylthio having in each case 6 to 10 carbon atoms or by a 5- to 7-membered, saturated or unsaturated heterocyclic radical having up to 3 hetero atoms from the series comprising S, N and O, it being possible for the cyclic radicals in turn to be substituted up to 3 times in an identical or different manner by halogen or cyano or by straight-chain or branched alkyl, alkoxy, alkylthio, alkoxycarbonyl, halogenoalkyl, halogenoalkoxy or halogenoalkylthio having in each case up to 4 carbon atoms, or the hydrocarbon radical is optionally substituted by a group of the formula $-CO_2-R^{17}$, $-CONR^{18}R^{19}$, $-NR^{20}R^{21}$, $NH-SO_2-X$ and/or $-NR^{22}-CO_2R^{23}$, wherein $R^{17}$ has the above-mentioned meaning of $R^{15}$ and is identical to or different from this and $R^{18}$, $R^{19}$, $R^{20}$, $R^{21}$, $R^{22}$ and $R^{23}$ have the above-mentioned meaning of $R^{11}$ and $R^{12}$ and are identical to or different from these, and X denotes phenyl, which is optionally substituted by methyl, $R^3$ represents cyano, nitro or formyl, or $R^3$ and $R^4$ together form a radical of the formula

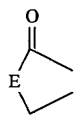

wherein

E denotes an oxygen or sulphur atom or the $-CH_2$-group, $R^5$ represents a cyclic, straight-chain or branched, saturated or unsaturated hydrocarbon radical having up to 12 carbon atoms, which is optionally interrupted up to twice in an identical or different manner by oxygen or sulphur, and which is optionally substituted up to 3 times in an identical or different manner by cycloalkyl having 3 to 8 carbon atoms, straight-chain or branched acyloxy having up to 4 carbon atoms, halogen, nitro, cyano or hydroxyl or by aryl, aryloxy or arylthio having in each case 6 to 10 carbon atoms or by a 5- to 7-membered, saturated or unsaturated optionally fused heterocyclic radical having up to 5 hetero atoms from the series comprising S, N and O, it being possible for the cyclic radicals in turn to be substituted up to 3 times in an identical or different manner by halogen, cyano, nitro or hydroxyl or by straight-chain or branched alkyl or alkoxy having in each case up to 4 carbon atoms, trifluoromethyl, trifluoromethoxy or trifluoromethylthio or by a group of the formula $-NR^{24}R^{25}$, wherein $R^{24}$ and $R^{25}$ have the abovementioned meaning of $R^{11}$ and $R^{12}$ and are identical to or different from these, or the hydrocarbon radical is optionally substituted by a group of the formula $-CO_2-R^{26}$, $-CONR^{27}R^{28}$, $-NR^{29}R^{30}$, $-NR^{31}-CO_2R^{32}$ or $-NR^{33}-SO_2R^{34}$, wherein $R^{26}$ has the abovementioned meaning of $R^{15}$ and is identical to or different from this and $R^{27}$, $R^{28}$, $R^{29}$, $R^{30}$, $R^{31}$, $R^{32}$, $R^{33}$ and $R^{34}$ have the above-mentioned meaning of $R^{11}$ and $R^{12}$ and are identical to or different from these, or $R^5$ represents a 5- to 7-membered, saturated or unsaturated heterocyclic radical having up to 4 hetero atoms from the series comprising S, N and O, which is optionally substituted up to 3 times in an identical or different manner by halogen, amino, cyano or nitro or by straight-chain or branched alkyl, alkoxy, alkylthio, alkoxycarbonyl, halogenoalkyl, halogenoalkoxy or halogenoalkylthio having in each case up to 4 carbon atoms or by $C_1$–$C_4$-mono- or -dialkylamino, or $R^5$ represents a group of the formula $D-R^{35}$, wherein D denotes the CO or $-S(O)_h$ group or an oxygen atom, wherein h denotes the number 0, 1 or 2, and $R^{35}$ denotes aryl having 6 to 10 carbon atoms or a 5- to 7-membered, saturated or unsaturated heterocyclic radical having up to 3 hetero atoms from the series comprising S, N and O, which is optionally substituted up to 3 times in an identical or different manner by halogen, amino, cyano or nitro or by straight-chain or branched alkyl, alkoxy, alkylthio, alkoxycarbonyl, halogenoalkyl, halogenoalkoxy or halogenoalkylthio having in each case up to 4 carbon atoms or by $C_1$–$C_4$-mono- or -dialkylamino, or $R^{35}$ denotes hydrogen or a cyclic, straight-chain or branched, saturated or unsaturated hydrocarbon radical having up to 8 carbon atoms, which is optionally interrupted by oxygen or sulphur, and which is optionally substituted by halogen or aryl, aryloxy or arylthio having in each case 6 to 10 carbon atoms or by a 5 - to 7-membered, saturated or unsaturated heterocyclic radical having up to 3 hetero atoms from the series comprising S, N and O, it being possible for the cyclic radicals in turn to be substituted by halogen, trifluoromethyl, methyl, methoxy, nitro or methylthio, or is substituted by a group of the formula $-NR^{36}R^{37}$ wherein $R^{36}$ and $R^{37}$ have the abovementioned meaning of $R^{11}$ and $R^{12}$ and are identical to or different from these, and salts thereof, with the proviso that $R^5$ may not represent optionally halogen-substituted pyridyl or thienyl.

Physiologically acceptable salts can be salts of the compounds according to the invention with inorganic or organic acids. Preferred salts are those with inorganic acids, such as, for example, hydrochloric acid, hydrobromic acid, phosphoric acid or sulphuric acid, or salts with organic carboxylic or sulphonic acids, such as, for example, acetic acid, maleic acid, fumaric acid, malic acid, citric acid, tartaric acid, lactic acid, benzoic acid or methanesulphonic acid, ethanesulphonic acid, phenylsulphonic acid, toluenesulphonic acid or naphthalenedisulphonic acid.

The compounds according to the invention exist in stereoisomeric forms which either behave as mirror images (enantiomers) or do not behave as mirror images (diastereomers). The invention relates both to antipodes and to racemic forms, as well as to the diastereomer mixtures. The racemic forms, like the diastereomers, can be separated into the stereoisomerically uniform constituents in a known manner (compare E. L. Eliel, Stereochemistry of Carbon Compounds, McGraw Hill, 1962).

Preferred compounds of the general formula (I) are those in which $R^1$ and $R^4$ are identical or different and represent hydrogen, amino, cyano, formyl or trifluoromethyl or represent straight-chain or branched alkyl having up to 4 carbon atoms, which is optionally substituted by hydroxyl or by a group of the formula —$NR^6R^7$, —O—CO—$R^8$, —O—$(CH_2)_a$—$OR^{8'}$ or —O—$(CH_2)_b$—$NR^9R^{10}$, wherein $R^6$, $R^7$, $R^9$ and $R^{10}$ are identical or different and denote hydrogen or straight-chain or branched alkyl having up to 4 carbon atoms, $R^8$ and $R^{8'}$ are identical or different and denote straight-chain or branched alkyl having up to 4 carbon atoms, and a and b are identical or different and denote the number 2, 3, 4 or 5, $R^2$ represents a group of the formula —$CONR^{11}R^{12}$ or —CO—A—$R^{13}$, wherein $R^{11}$ and $R^{12}$ are identical or different and denote hydrogen or a straight-chain, branched or cyclic, saturated or unsaturated hydrocarbon radical having up to 6 carbon atoms, which is optionally substituted by fluorine, chlorine, hydroxyl, phenyl or pyridyl, it being possible for the cyclic radicals in turn to be substituted by fluorine or chlorine or by alkyl, alkoxy, alkylthio or alkoxycarbonyl having in each case up to 2 carbon atoms, trifluoromethyl or trifluoromethoxy, or denote phenyl or pyridyl, which are optionally substituted by fluorine or chlorine or by alkyl, alkoxy, alkylthio or alkoxycarbonyl having in each case up to 2 carbon atoms, trifluoromethyl or trifluoromethoxy, or $R^{11}$ and $R^{12}$, together and including the nitrogen atom, form a 3- to 8-membered, saturated or unsaturated heterocyclic radical which can optionally be interrupted by an oxygen atom or by a radical of the formula $S(O)_d$, —CO— or wherein d denotes the number 0, 1 or 2, $R^{15}$ denotes hydrogen or phenyl, which is optionally substituted by fluorine, chlorine, methyl, ethyl, methoxy, ethoxy, trifluoromethyl or trifluoromethoxy, or denotes a cyclic, straight-chain or branched, saturated or unsaturated hydrocarbon radical having up to 4 carbon atoms, which is optionally substituted by chlorine, fluorine or phenyl or by a 5-to 7-membered, saturated or unsaturated heterocyclic radical having up to 3 hetero atoms from the series comprising S, N and O, it being possible for the cyclic radicals in turn to be substituted by fluorine, chlorine, methyl, methoxy, methylthio, trifluoromethyl or trifluoromethoxy, A denotes a direct bond or an oxygen atom, $R^{13}$ denotes hydrogen, phenyl or pyridyl, which are optionally substituted by fluorine, chlorine, methyl, methoxy, methylthio, trifluoromethyl or trifluoromethoxy, or denotes a cyclic, straight-chain or branched, saturated or unsaturated hydrocarbon radical having up to 8 carbon atoms, which is optionally interrupted up to twice in an identical or different manner by oxygen or by —CO—, —CO—NH—, —O—CO—, —CO—O—, —NH—CO—, —$SO_2$—NH—, —NH—$SO_2$—, —$S(O)_e$— or —$NR^{16}$—, wherein e has the abovementioned meaning of d and is identical to or different from this, $R^{16}$ has the abovementioned meaning of $R^{15}$ and is identical to or different from this, or the hydrocarbon radical is optionally interrupted up to twice in an identical or different manner by arylidene having 6 to 10 carbon atoms or heterocyclic radicals of the formulae

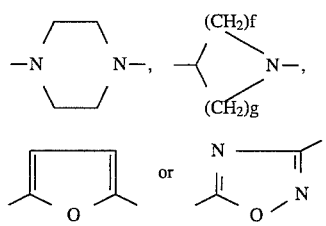

wherein f and g are identical or different and denote the number 1 or 2, and the hydrocarbon radical is optionally substituted up to twice in an identical or different manner by cyclopropyl, cyclobutyl, cyclopentyl, cyclohexyl, fluorine, chlorine, nitro, cyano, hydroxyl, —O—$NO_2$ or straight-chain or branched alkylthio, alkoxy or acyloxy having in each case up to 4 carbon atoms or by phenyl, phenoxy, phenylthio or pyridyl, it being possible for the cyclic radicals in turn to be substituted by fluorine, chlorine, cyano, methyl, methoxy, methylthio, trifluoromethyl or trifluoromethoxy, or the hydrocarbon radical is optionally substituted by a group of the formula —$CO_2$—$R^{17}$, —$CONR^{18}R^{19}$, —$NR^{20}R^{21}$, —NH—$SO_2$—X and/or —$NR^{22}$—$CO_2R^{23}$, wherein $R^{17}$ has the abovementioned meaning of $R^{15}$ and is identical to or different from this and $R^{18}$, $R^{19}$, $R^{20}$, $R^{21}$, $R^{22}$ and $R^{23}$ have the abovementioned meaning of $R^{11}$ and $R^{12}$ and are identical to or different from these, and X denotes phenyl, which is optionally substituted by methyl, $R^3$ represents cyano, nitro or formyl, or $R^3$ and $R^4$ together form a radical of the formula

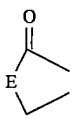

wherein

E denotes an oxygen or sulphur atom or the —CH$_2$-group, $R^5$ represents a cyclic, straight-chain or branched, saturated or unsaturated hydrocarbon radical having up to 10 carbon atoms, which is optionally interrupted by oxygen or sulphur, and which is optionally substituted up to twice in an identical or different manner by cyclopropyl, cyclobutyl, cyclopentyl, cyclohexyl, fluorine, chlorine, bromine, acyloxy having up to 2 carbon atoms, cyano or hydroxyl or by phenyl, phenyloxy or phenylthio or by a 5- to 7-membered, saturated or unsaturated heterocyclic radical having up to 3 hetero atoms from the series comprising S, N and O, it being possible for the phenyl and the heterocyclic radicals in turn to be substituted up to twice in an identical or different manner by fluorine, chlorine, bromine, hydroxyl, methyl, ethyl, methoxy, ethoxy, trifluoromethyl, trifluoromethoxy or trifluoromethylthio or by a group of the formula —NR$^{24}$R$^{25}$, wherein $R^{24}$ and $R^{25}$ have the abovementioned meaning of $R^{11}$ and $R^{12}$ and are identical to or different from these, or the hydrocarbon radical is optionally substituted by a group of the formula —CO$_2$R$^{26}$, —CONR$^{27}$R$^{28}$, —NR$^{29}$R$^{30}$, —NR$^{31}$—CO$_2$R$^{32}$ or —NR$^{33}$-SO$_2$R$^{34}$
wherein $R^{26}$ has the abovementioned meaning of $R^{15}$ and is identical to or different from this
and $R^{27}$, $R^{28}$, $R^{29}$, $R^{30}$, $R^{31}$, $R^{32}$, $R^{33}$ and $R^{34}$ have the above-mentioned meaning of $R^{11}$ and $R^{12}$ and are identical to or different from these, or $R^5$ represents a 5- to 7-membered, saturated or unsaturated heterocyclic radical having up to 4 hetero atoms from the series comprising S, N and O, which is optionally substituted up to twice in an identical or different manner by fluorine, chlorine, bromine, cyano or nitro or by alkyl, alkoxy, alkylthio, alkoxycarbonyl, halogenoalkyl, halogenoalkoxy or halogenoalkylthio having in each case up to 2 carbon atoms or amino or by C$_1$–C$_4$-mono- or -dialkylamino, or $R^5$ represents a group of the formula D—R$^{35}$,
wherein D denotes the CO or —S(O)$_h$ group or an oxygen atom,
wherein h denotes the number 0, 1 or 2,
and $R^{35}$ denotes phenyl or a 5- to 7-membered, saturated or unsaturated heterocyclic radical having up to 3 hetero atoms from the series comprising S, N and O, which are optionally substituted up to twice in an identical or different manner by fluorine, chlorine, bromine, cyano or nitro or by straight-chain or branched alkyl, alkoxy, alkylthio, alkoxycarbonyl, halogenoalkyl, halogenoalkoxy or halogenoalkylthio having in each case up to 4 carbon atoms or amino or by C$_1$–C$_4$-mono- or -dialkylamino, or $R^{35}$ denotes hydrogen or a cyclic, straight-chain or branched, saturated or unsaturated hydrocarbon radical having up to 8 carbon atoms, which is optionally interrupted by oxygen or sulphur, and which can optionally be substituted by fluorine, chlorine, phenyl, phenoxy or phenylthio, or is substituted by a group of the formula —NR$^{36}$R$^{37}$,
wherein $R^{36}$ and $R^{37}$ have the abovementioned meaning of $R^{11}$ and $R^{12}$ and are identical to or different from these,
and salts thereof, with the proviso that $R^5$ may not represent optionally halogen-substituted pyridyl or thienyl.

Particularly preferred compounds of the general formula (I) are those
in which $R^1$ and $R^4$ are identical or different and represent hydrogen, amino, trifluoromethyl, methyl or ethyl, $R^2$ represents a group of the formula —CO—NR$^{11}$R$^{12}$ or —CO—A—R$^{13}$
wherein $R^{11}$ and $R^{12}$ are identical or different and denote hydrogen or a straight-chain, branched or cyclic, saturated or unsaturated hydrocarbon radical having up to 6 carbon atoms, or denote phenyl, which is optionally substituted by fluorine, chlorine, methyl or methoxy, A denotes a direct bond or an oxygen atom, $R^{13}$ denotes hydrogen a cyclic, straight-chain or branched, saturated or unsaturated hydrocarbon radical having up to 8 carbon atoms, which is optionally interrupted by oxygen or sulphur or by —CO—NH—, —O—CO—, —CO—O—, —NH—CO—, —SO$_2$—NH—, —NH—SO$_2$— or —NR$^{16}$,
wherein $R^{16}$ denotes hydrogen or straight-chain or branched alkyl having up to 4 carbon atoms, or the hydrocarbon radical is interrupted by heterocyclic radicals of the formulae

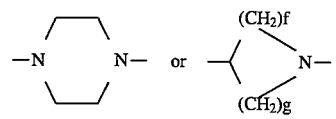

in which f and g are identical or different and denote the number 1 or 2, and the hydrocarbon radical is optionally substituted by cyclopropyl, cyclobutyl, cyclopentyl, cyclohexyl, fluorine, chlorine, nitro, cyano or hydroxyl or by phenyl, phenoxy, phenylthio or pyridyl, which can in turn be substituted by fluorine, chlorine, methyl, methoxy, methylthio, trifluoromethyl or trifluoromethoxy, or the hydrocarbon radical is optionally substituted by a group of the formula —CO$_2$R$^{17}$, —CONR$^{18}$R$^{19}$, —NR$^{20}$R$^{21}$, —NH—SO$_2$—X and/or —NR$^{22}$—CO$_2$R$^{23}$,
wherein $R^{20}$ and $R^{21}$ are identical or different and denote hydrogan or a straight-chain, branched or cyclic, saturated or unsaturated hydrocarbon radical having up to 6 carbon atoms, which is optionally substituted by fluorine, chlorine, pyridyl or phenyl, which can in turn be substituted by fluorine, chlorine, methyl or methoxy, or denotes phenyl, which is optionally substituted by fluorine, chlorine, methyl or methoxy, or $R^{20}$ and $R^{21}$, together and including the nitrogen atom, form a 5- to 6-membered, saturated or unsaturated heterocyclic radical, which can optionally contain up to 2 further hetero atoms from the series comprising S, N and O and which is optionally also substituted by straight-chain or branched alkyl having up to 4 carbon atoms, benzyl or phenyl, X denotes phenyl, which is optionally substituted by methyl, $R^{17}$, $R^{18}$, $R^{19}$, $R^{22}$ and $R^{23}$ are identical or different and denote hydrogen or straight-chain or branched alkyl having up to 6 carbon atoms, which is optionally substituted by phenyl, or denote phenyl which is optionally substituted by fluorine, chlorine or bromine, $R^3$ represents cyano, nitro or formyl, or $R^3$ and $R^4$ together form a radical of the formula

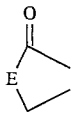

wherein

E denotes an oxygen or sulphur atom or the —$CH_2$-group, $R^5$ represents a cyclic, straight-chain or branched, saturated or unsaturated hydrocarbon radical having up to 8 carbon atoms, which is optionally interrupted by oxygen or sulphur, and which is optionally substituted by cyclopropyl, cyclobutyl, cyclopentyl, cyclohexyl, fluorine, chlorine, nitro, cyano, hydroxyl or by phenyl, phenyloxy or phenylthio or by a 5- to 7-membered, saturated or unsaturated heterocyclic radical having up to 2 hetero atoms from the series comprising S, N and O, it being possible for the phenyl rings and heterocyclic radicals in turn to be substituted up to twice in an identical or different manner by fluorine, chlorine, methyl, methoxy, trifluoromethyl or trifluoromethoxy or by a group of the formula —$NR^{24}R^{25}$, wherein $R^{24}$ and $R^{25}$ have the abovementioned meaning of $R^{11}$ and $R^{12}$ and are identical to or different from these, or the hydrocarbon radical is optionally substituted by a group of the formula —$CO_2$—$R^{26}$, —$CONR^{27}R^{28}$, —$NR^{29}R^{30}$, —$NR^{31}$—$CO_2R^{32}$ or —$NR^{33}$—$SO_2R^{34}$, wherein $R^{26}$ denotes alkyl having 1–4 C atoms or phenyl, and $R^{27}$, $R^{28}$, $R^{29}$, $R^{30}$, $R^{31}$, $R^{32}$, $R^{33}$ and $R^{34}$ have the above-mentioned meaning of $R^{11}$ and $R^{12}$ and are identical to or different from these, or $R^5$ represents a 5- to 6-membered, saturated or unsaturated heterocyclic radical having up to 2 hetero atoms from the series comprising S, N and O, which is optionally substituted by fluorine, chlorine, methyl, methoxy, methylthio or trifluoromethyl, or $R^5$ represents a group of the formula D—$R^{35}$, wherein D denotes the —$S(O)_h$ group or an oxygen atom, wherein h denotes the number 0, 1 or 2, and $R^{35}$ denotes phenyl, which is optionally substituted by fluorine, chlorine, bromine, methyl, methoxy, methylthio, trifluoromethyl or amino or by $C_1$–$C_2$-mono- or -dialkylamino, or $R^{35}$ denotes hydrogen or a cyclic, straight-chain or branched, saturated or unsaturated hydrocarbon radical having up to 6 carbon atoms, which is optionally interrupted by oxygen or sulphur, and which is optionally substituted by fluorine, chlorine or phenyl, or is substituted by a group of the formula —$NR^{36}R^{37}$, wherein $R^{36}$ and $R^{37}$ have the abovementioned meaning of $R^{11}$ and $R^{12}$ and are identical to or different from these, and salts thereof, with the proviso that $R^5$ may not represent optionally halogen-substituted pyridyl or thienyl.

Especially preferred compounds of the general formula (I) are those in which $R^1$ represents hydrogen, methyl, ethyl, trifluoromethyl or amino, $R^4$ represents hydrogen, methyl or amino, $R^2$ represents a group of the formula —CO—$NR^{11}R^{12}$ or —CO—A—$R^{13}$, wherein $R^{11}$ and $R^{12}$ are identical or different and denote hydrogen or a straight-chain, branched or cyclic, saturated or unsaturated hydrocarbon radical having up to 6 carbon atoms, A denotes a direct bond or an oxygen atom, $R^{13}$ denotes hydrogen or a cyclic, straight-chain or branched, saturated or unsaturated hydrocarbon radical having up to 8 carbon atoms, which is optionally interrupted by oxygen or sulphur or by —O—CO—, —CO—O— or —$NR^{16}$, wherein $R^{16}$ denotes hydrogen or methyl and the hydrocarbon radical is optionally substituted by cyclopropyl, cyclobutyl, cyclopentyl, cyclohexyl, fluorine, chlorine, nitro, cyano, hydroxyl, —O—$NO_2$ or by phenyl, phenoxy, phenylthio or pyridyl, which can in turn be substituted by fluorine, chlorine, methyl, methoxy, methylthio, trifluoromethyl or trifluoromethoxy, or the hydrocarbon radical is optionally substituted by a group of the formula —$CO_2$—$R^{17}$, —NH—$SO_2$—X and/or —$NR^{20}R^{21}$ wherein $R^{17}$ denotes hydrogen, methyl or ethyl, $R^{20}$ and $R^{21}$ are identical or different and denote hydrogen or a straight-chain, branched or cyclic, saturated or unsaturated hydrocarbon radical having up to 5 carbon atoms, which is optionally substituted by phenyl, which in turn can be substituted by fluorine, chlorine, methyl or methoxy, or $R^{20}$ and $R^{21}$, together and including the nitrogen atom, form a piperidine or piperazine ring, which can optionally be substituted by methyl, ethyl, phenyl or benzyl, X denotes phenyl, which is optionally substituted by methyl, $R^3$ represents cyano or nitro, or $R^3$ and $R^4$ together form a radical of the formula

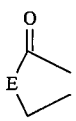

wherein

E denotes an oxygen or sulphur atom or the —$CH_2$- group, $R^5$ represents a cyclic, straight-chain or branched, saturated or unsaturated hydrocarbon radical having up to 6 carbon atoms, which is optionally interrupted by oxygen or sulphur,
and which is optionally substituted by cyclopropyl, cyclobutyl, cyclopentyl, cyclohexyl, fluorine, chlorine, cyano or hydroxyl or by phenyl, phenyloxy or phenylthio or by a 5- to 7-membered, saturated or unsaturated heterocyclic radical having up to 2 hetero atoms from the series comprising S, N and O, it being possible for the cyclic radicals in turn to be substituted by fluorine, chlorine, methyl, methoxy, trifluoromethyl or trifluoromethoxy or by a group of the formula —$NR^{24}R^{25}$, wherein $R^{24}$ and $R^{25}$ denote hydrogen, phenyl, benzyl or straight-chain or branched alkyl having up to 4 carbon atoms, or the hydrocarbon radical is optionally substituted by a group of the formula —$NR^{29}R^{30}$, wherein $R^{29}$ and $R^{30}$ are identical or different and denote hydrogen, phenyl or straight-chain or branched alkyl having up to 4 carbon atoms, which is optionally substituted by phenyl, or $R^5$ represents a 5- to 6-membered, saturated or unsaturated heterocyclic radical having up to 2 hetero atoms from the series comprising S, N and O, which is optionally substituted by fluorine, chlorine, methyl, methoxy, methylthio or trifluoromethyl, or $R^5$ represents a group of the formula D—$R^{35}$, wherein D denotes an oxygen or sulphur atom, and $R^{35}$ denotes phenyl, which is optionally substituted by fluorine, chlorine, methyl, methoxy, methylthio, trifluoromethyl or amino or by $C_1$–$C_2$-mono- or -dialkylamino, or $R^{35}$ denotes hydrogen or a cyclic, straight-chain or branched, saturated or unsaturated hydrocarbon radical having up to 6 carbon atoms, which is optionally substituted by fluorine, chlorine or phenyl, and salts thereof, with the proviso that $R^5$ my not represent optionally halogen-substituted pyridyl or thienyl.

A process has furthermore been found for the preparation of the compounds of the general formula (I) according to the invention, characterized in that in the case where $R^3$ represents cyano, nitro or formyl,

[A] compounds of the general formula (II)

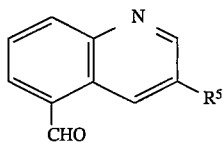

(II)

in which $R^5$ has the abovementioned meaning, are first reacted with acyl compounds of the general formula (III)

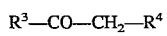

$R^3$—CO—$CH_2$—$R^4$ (III)

in which $R^3$ and $R^4$ have the abovementioned meaning, if appropriate with isolation of the xylidene compounds of the general formula (IV)

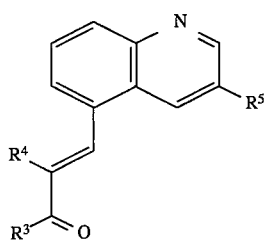

(IV)

in which $R^3$, $R^4$ and $R^5$ have the abovementioned meaning, and the products are then reacted with compounds of the formula (V)

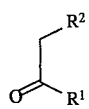

(V)

in which $R^1$ and $R^2$ have the abovementioned meaning, and a reactive ammonium compound, for example ammonium acetate, or directly with enamino compounds of the general formula (VI)

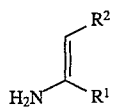

(VI)

in which $R^1$ and $R^2$ have the abovementioned meaning, in inert solvents, or

[B] compounds of the general formula (II) are first reacted with compounds of the general formula (V), if appropriate with isolation of the ylidene compounds of the general formula (VII)

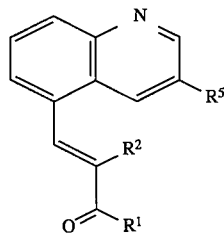

(VII)

in which $R^1$, $R^2$ and $R^5$ have the abovementioned meaning,
and the products are then reacted either with compounds of the general formula (III) in the presence of ammonium compounds or directly with compounds of the general formula (VIII)

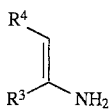 (VIII)

in which
R³ and R⁴ have the abovementioned meaning,
or
[C] in the case where R³ and R⁴ together form a radical of the formula

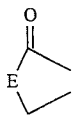

wherein
E' represents an oxygen or sulphur atom, compounds of the general formula (IX)

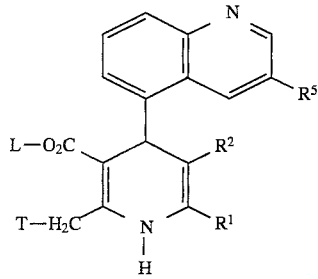 (IX)

in which
R¹, R² and R⁵ have the abovementioned meaning,
L represents $C_1$-$C_4$-alkyl
and
T represents $C_1$-$C_4$-acyloxy or acylthio,
are first prepared by the methods described under [A] and [B] and basic or acid cyclization is then carried out by known methods,
or
[D] in that, in the case where E represents the —CH₂- group,
compounds of the general formula (II) are first reacted with acyl compounds of the general formula (X)

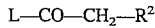 (X)

in which
R² has the abovementioned meaning
and
L has the abovementioned meaning of R¹, and in the case of the hydroxyl and/or amino functions, these are optionally present in protected form, if appropriate with isolation of the ylidene compounds of the general formula (XI)

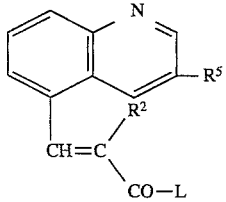 (XI)

in which
R², R⁵ and L have the abovementioned meaning, and the products are then reacted with a compound of the formula

 (XII)

and a reactive ammonium compound, for example ammonium acetate, if appropriate with isolation of the intermediate products of the general formula (XIII)

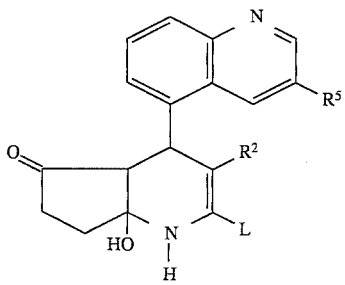 (XIII)

in which
R², R³ and L have the abovementioned meaning,
in inert solvents,
and water is subsequently separated off in a last step, if appropriate in the presence of an auxiliary.

The processes according to the invention can be illustrated byway of example by the following equation:

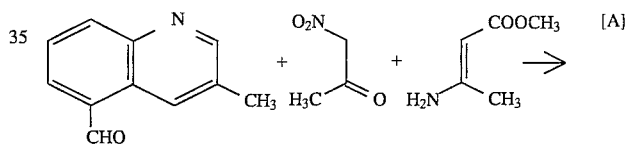 [A]

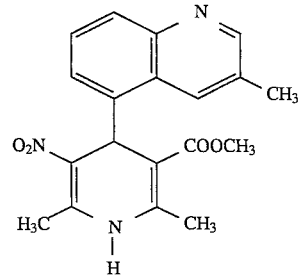

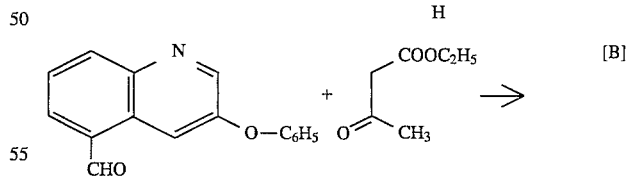 [B]

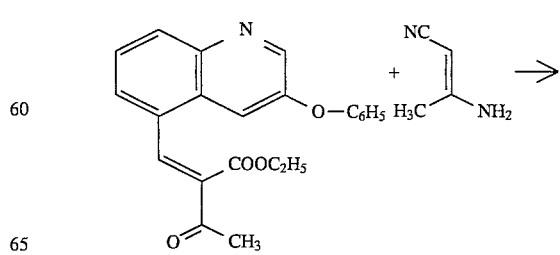

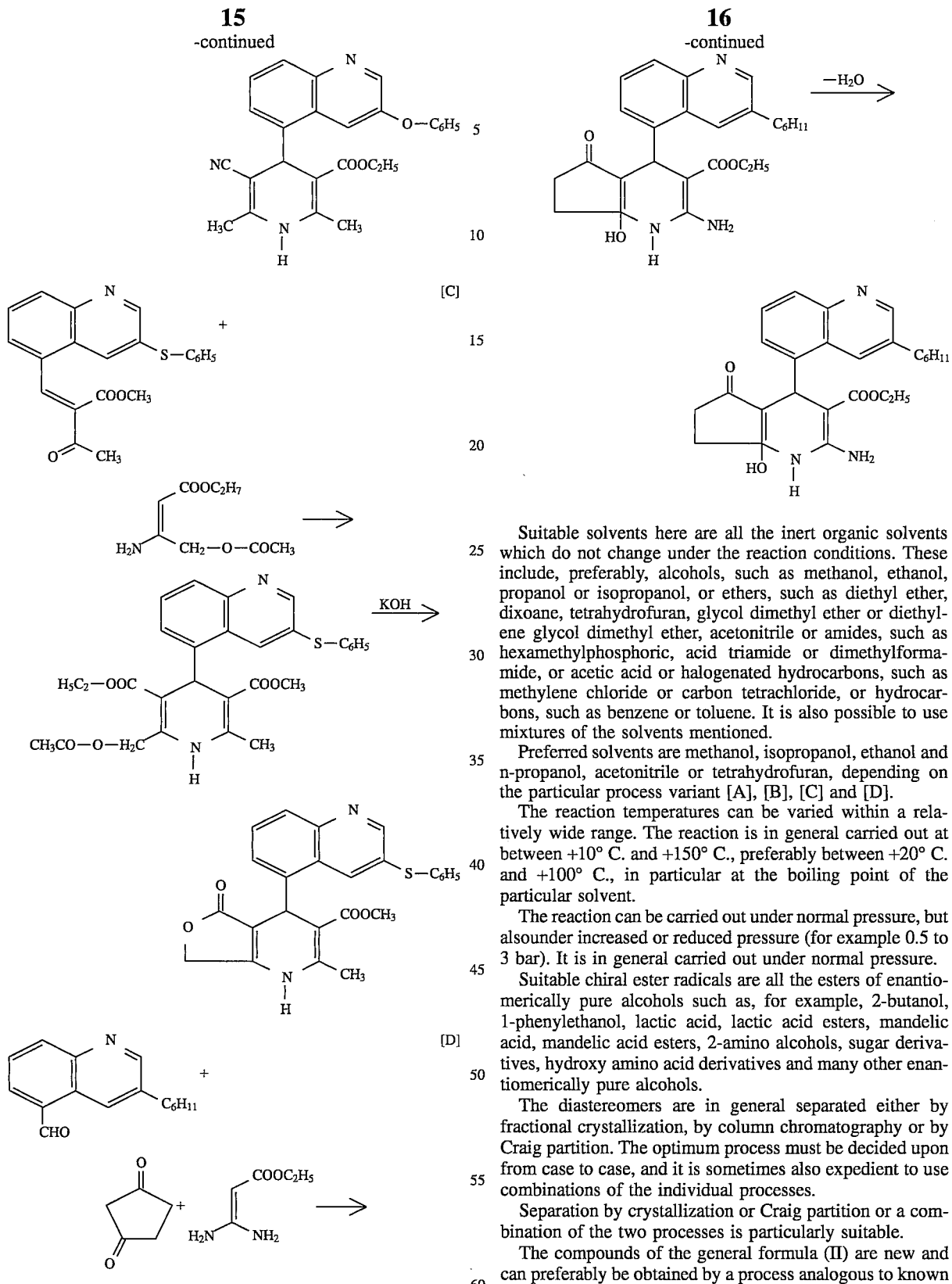

Suitable solvents here are all the inert organic solvents which do not change under the reaction conditions. These include, preferably, alcohols, such as methanol, ethanol, propanol or isopropanol, or ethers, such as diethyl ether, dixoane, tetrahydrofuran, glycol dimethyl ether or diethylene glycol dimethyl ether, acetonitrile or amides, such as hexamethylphosphoric, acid triamide or dimethylformamide, or acetic acid or halogenated hydrocarbons, such as methylene chloride or carbon tetrachloride, or hydrocarbons, such as benzene or toluene. It is also possible to use mixtures of the solvents mentioned.

Preferred solvents are methanol, isopropanol, ethanol and n-propanol, acetonitrile or tetrahydrofuran, depending on the particular process variant [A], [B], [C] and [D].

The reaction temperatures can be varied within a relatively wide range. The reaction is in general carried out at between +10° C. and +150° C., preferably between +20° C. and +100° C., in particular at the boiling point of the particular solvent.

The reaction can be carried out under normal pressure, but alsounder increased or reduced pressure (for example 0.5 to 3 bar). It is in general carried out under normal pressure.

Suitable chiral ester radicals are all the esters of enantiomerically pure alcohols such as, for example, 2-butanol, 1-phenylethanol, lactic acid, lactic acid esters, mandelic acid, mandelic acid esters, 2-amino alcohols, sugar derivatives, hydroxy amino acid derivatives and many other enantiomerically pure alcohols.

The diastereomers are in general separated either by fractional crystallization, by column chromatography or by Craig partition. The optimum process must be decided upon from case to case, and it is sometimes also expedient to use combinations of the individual processes.

Separation by crystallization or Craig partition or a combination of the two processes is particularly suitable.

The compounds of the general formula (II) are new and can preferably be obtained by a process analogous to known processes, by a procedure in which 4-amino-3-hydroxyphthalide of the formula (XIV)

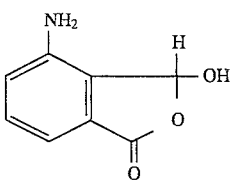

(XIV)

is cyclized, either after isolation or directly in situ after hydrogenation of 4-nitro-3-hydroxyphthalide of the formula (XV)

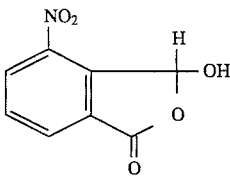

(XV)

with compounds of the general formula (XVI)

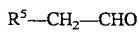

(XVI)

to give compounds of the general formula (XVII)

(XVII)

these are then converted with the customary reducing agents, such as, for example, lithium aluminium hydride, or via a mixed anhydride with sodium borohydride, into the alcohols of the general formula (XVIII)

(XVIII)

and these are then oxidized, either after isolation or directly in situ, with oxidizing agents, such as, for example, manganese dioxide, to give compounds of the general formula (II),
wherein
$R^5$ in each case has the abovementioned meaning.

The process can be illustrated by the following equation:

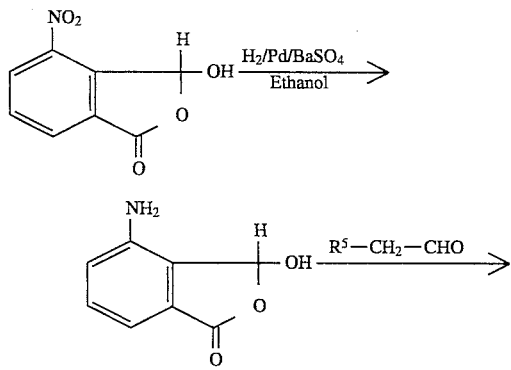

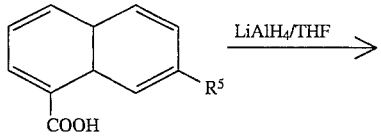

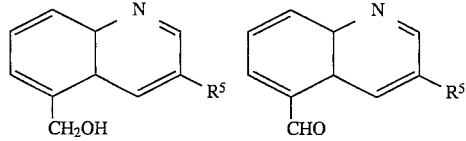

The acyl compounds of the general formula (III) and (X) are known or can be prepared by customary methods.

The compounds of the general formulae (V), (VI), (VIII) and (XII) are known.

The ylidene compounds (IV), (VII) and (XI) are new, but can be prepared by customary methods.

The compounds of the general formula (IX) are new, but can be prepared by known methods, for example by reacting benzylidene compounds of the general formula (IV) with chloroacetic acid esters and ammonium compounds.

The compounds of the general formula (XIII) are new and can be prepared as described above.

The above preparation processes are given merely for illustration. The preparation of the compounds of the formula (I) is not limited to these processes, but any modification of these processes can be used in the same manner for preparation of the compounds according to the invention.

The compounds according to the invention display an unforeseeable, valuable pharmacological action spectrum. They influence the contractility of the heart and the tone of the smooth muscle, and in particular they display positively inotropic actions. They can therefore be employed in medicements for influencing pathologically altered blood pressure, as coronary therapeutics and for the treatment of cardiac insufficiency. They can furthermore be used for the treatment of disturbances in cardiac rhythm, for lowering blood sugar, for detumescence of mucosaand for influencing the salt and fluid balance.

The cardiac and vascular actions were found on the isolated perfused hearts of guinea-pigs. The hearts of guinea-pigs weighing 250 to 350 g are used for this. The animals are sacrificed by a blow to the head, the thorax is opened and a metal cannula is inserted into the exposed aorta. The heart is removed with the lungs from the thorax and connected to the perfusion apparatus, with perfusion running, via an aortic cannula. The lungs are removed at the lung roots and the perfusion medium used is a Krebs-Henseleit solution (118.5 mmol/l of NaCl, 4.75 mmol/l of KCl, 1.19 mmol/l of $KH_2PO_4$, 1.19 mmol/l of $MgSO_4$, 25 mmol/l of $NaHCO_3$, 0.013 mmol/l of $Na_2EDTA$), the $CaCl_2$ content of which is 1.2 mmol/l. 10 mmol/l of glucose are added as energy-supplying substrate, and the solution is filtered particle-free before the perfusion. The solution is gassed with carbogen (95% $O_2$, 5% $CO_2$) to maintain the pH at 7.4. The hearts are perfused with a constant flow rate (10 ml/minute) at 32° C. by means of a roller squeezing pump.

To measure the cardiac function, a latex balloon which is filled with liquid and connected to a pressure transducer via a column of liquid is inserted through the left auricle into the left ventricle and the isovolumetric contractions are recorded on a high-speed recorder. The perfusion pressure is recorded by means of a pressure transducer connected to the perfusion system before the heart. Under these conditions, a reduction in the perfusion pressure indicates coronary dilation and an increase or decrease in the left ventricular contraction amplitude indicates a reduction or, respectively, an increase in cardiac contractility. The compounds according to the invention are perfused into the perfusion system in suitable dilutions shortly before the isolated heart.

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents end/or excipients, if appropriate using emulsifying agents and/or dispersing agents, and, for example, in the case where water is used as the diluent, organic solvents can be used as auxiliary solvents if appropriate.

Administration is effected in the customary manner, preferably orally or parenterally, in particular perlingually or intravenously.

In general, it has proved advantageous in the case of intravenous administration to administer amounts of about 0.001 to 1 mg/kg, preferably about 0.01 to 0.5 mg/kg of body weight in order to achieve effective results, and in the case of oral administration the dosage is about 0.01 to 20 mg/kg, preferably 0.1 to 10 mg/kg of body weight.

Nevertheless, it may at times be necessary to deviate from the amounts mentioned, and in particular as a function of the body weight or of the nature of the administration route, of the behaviour of the individual towards the medicament, of the nature of the formulation thereof and of the time or interval at which administration takes place. Thus in some cases it may suffice to manage with less than the abovementioned minimum amount, while in other cases the upper limit mentioned must be exceeded. Where relatively large amounts are administered, it may be advisable to divide these into several individual doses over the course of the day.

STARTING COMPOUNDS

Example I

Ethyl 4-acetoxy-2- (3-phenoxy-quinolin-5-ylidene)-3-oxobutyrate

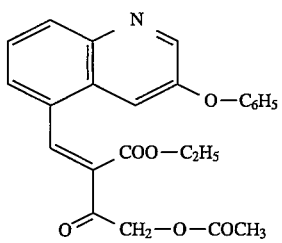

2.49 g (10 mmol) of 3-phenoxyquinoline-5-aldehyde are heated under reflux in 30 ml of methylene chloride with 2.07 g (11 mmol) of ethyl 4-acetoxyacetate, 0.05 ml of acetic acid and 0.1 ml of piperidine overnight, using a water separator. The mixture is cooled, washed twice with water and concentrated. 4.2 g of a yellowish oil are obtained.

Example II

Phenylthioacetaldehyde

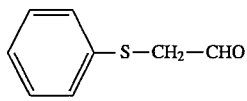

23 g (1 mol) of sodium are dissolved in 400 ml of ethanol. After cooling, 110 g (1 mol) of thiophenol are added. 197 g (1 mol) of bromoacetaldehyde diethyl acetal are added dropwise to this mixture. The mixture is heated under reflux for 24 hours and cooled and the salt which has precipitated out is filtered off with suction. The filtrate is concentrated, water is added to the evaporation residue and the mixture is extracted 3 times with ether. The combined ether phases are washed with 1 N sodiumhydroxide solution and water, dried and concentrated. The evaporation residue obtained is dissolved in 1.2 l of tetrahydrofuran, 1 l of dilute hydrochloric acid is added and the mixture is heated under reflux for 3 hours. It is cooled, diluted with water and extracted 3 times with ether, and the combined ether phases are washed with water, sodium bicarbonate solution and water again, dried and concentrated. 150 g of crude oil are obtained, which is reacted without further purification.

Example III

3 - Phenylthio-quinoline-5-carboxylic acid

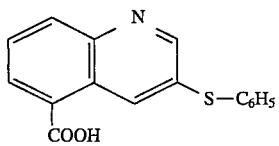

100 g (0,512 mol) of 3-hydroxy-4-nitro-phthalide are hydrogenated in 500ml of ethanol, after addition of 10 g of Pd/barium sulphate, under 3.5 bar, during which the temperature may rise to 50° C. The mixture is filtered while hot with suction. 75 g (0.5 mol) of the compound from Example II are introduced into the filtrate and the mixture is heated under reflux overnight. After cooling, the product which has precipitated out is filtered off with suction and washed with ethanol. 35 g of a virtually colourless compound of melting point 287°–289° C. are obtained.

Example IV

5-Hydroxymethyl-3-phenylthio-quinoline

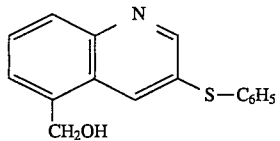

28.1 g (0.1 mol) of the compound from Example III are dissolved in 800 ml of dry tetrahydrofuran, and 200 ml of a 1 molar solution of lithium aluminium hydride in tetrahydrofuran are added dropwise at 20°–30° C. The mixture is stirred at room temperature for 3 hours. 8 ml of water and 24 ml of dilute potassium hydroxide solution are added dropwise in succession, while cooling with ice. The mixture is subsequently stirred for 1 hour and filtered with suction over Celite, and the residue is rinsed with tetrahydrofuran. After the filtrate has been concentrated, 27 g of crude

Example V

3-Phenylthio-quinoline-5-aldehyde

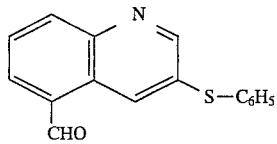

27 g of the compound from Example IV are dissolved in a mixture of 500 ml of dimethoxyethane and 500 ml of methylene chloride, and 165 g of manganese dioxide are added. The mixture is stirred at room temperature for 2 hours and filtered with suction over Celite, and the residue is washed with methylene chloride. After the filtrate has been concentrated, the evaporation residue obtained is purified by flash chromatography with toluene/ethyl acetate mixtures. 13.7 g of virtually colourless crystals of melting point 46°–47° C. are obtained.

Example VI

3-Cyclohexyl-quinoline-5-carboxylic acid

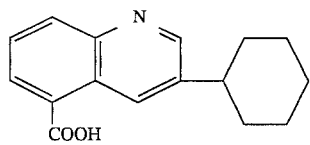

A mixture of 50 g of 4-nitro-3-hydroxyphthalide in 200 ml of isopropanol is hydrogenated with 5 g of Pd/barium sulphate under 3.5 bar, during which the temperature rises to 55° C. When the hydrogenation has ended (about 30 minutes), the catalyst is filtered off hot with suction. 33 g (260 mmol) of cyclohexylacetaldehyde are added to the filtrate and, after addition of a catalytic amount of sodium methylate, the mixture is heated under reflux for 20 hours. After cooling, the crystals which have precipitated out are filtered off with suction and washed with isopropanol. 15 g of virtually colourless product with a melting point of over 280° C. are obtained.

Example VII

3-Cyclohexyl-5-hydroxymethyl-quinoline

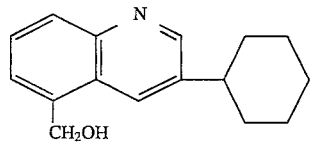

33.6 g (131.7 mmol) of the compound from Example VI are dissolved in 320 ml of dimethoxyethane and the solution is stirred with 197.6 mmol (27.6 ml) of triethylamine. After 30 minutes, 19.75 ml (197.5 mmol) of ethyl chlorocarbonate are added dropwise at 20°–30° C. The mixture is subsequently stirred for 30 minutes and the salt is filtered off with suction and washed with dimethoxyethane. The filtrate is concentrated and the residue is dissolved in a mixture of 320 ml of ethanol and 160 ml of water, and a solution of 9.25 g of sodium borohydride in 54 ml of water is added dropwise at 15°–18° C. The mixture is stirred at room temperature for 1 hour and the salt is filtered off with suction and washed with ethanol and water. The filtrate is concentrated to one third, methylene chloride and water are added and the phases are separated. The organic phase is washed 3 times with water, dried and concentrated. 26 g of a pale brown oil are obtained, which is employed without further purification.

Example VIII

3-Cyclohexyl-quinoline-5-aldehyde

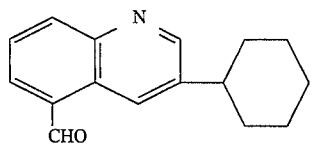

150 g of manganese dioxide are added to 26 g of the compound VII in 260 ml of methylene chloride. The mixture is stirred for 1 hour and the precipitate is filtered off with suction and washed with methylene chloride. The filtrate is concentrated. 20 g of a crystalline compound which has a melting point of 94°–95° C. after recrystallization from acetonitrile are obtained.

PREPARATION EXAMPLES

Example 1

Isopropyl 3-cyano-1,4-dihydro-2,6-dimethyl-4-(3-benzylquinolin-5-yl)-pyridine-5-carboxylate

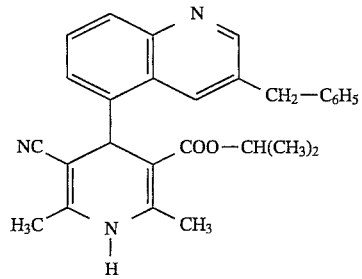

0.72 g of isopropyl acetoacetate, 0.025 ml of acetic acid and 0.05 ml of piperidine are added to 1.24 g (5 mmol) of 3-benzylquinoline-5-aldehyde in 20 ml of methylene chloride and the mixture is heated at the boiling point overnight. It is cooled, diluted with methylene chloride, extracted twice by shaking with water, dried and concentrated. The resulting intermediate product is suspended in 15 ml of isopropanol, 0.41 g (5 mmol) of 3-aminocrotononitrile are added and the mixture is stirred at 80° C. for 20 hours. It is concentrated and the residue is purified by flash chromatography with toluene/ethyl acetate mixtures. After crystallization from ethanol/ether 1:1, 1.0 g of colourless crystals of melting point 188°–190° C. is obtained.

Example 2

Ethyl 2-methyl-4-(3-phenoxy-quinoline-5-yl)-5-oxo-1,4,5,7-tetrahydrofuran [3,4-b]pyridine -3-carboxylate

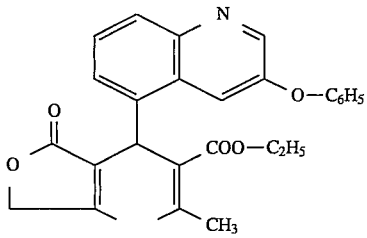

a) Preparation of the starting compound
Diethyl 2-acetoxy-6-methyl-4-(3-phenoxy-quinoline-5-yl)-1,4-dihydropyridine-3,5-dicarboxylate

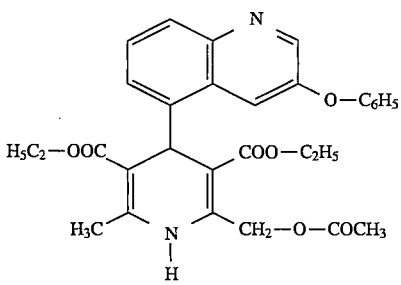

4.2 g (10 mmol) of the compound from Example 1 are boiled under reflux in 50 ml of isopropanol with 1.4 g (11 mmol) of ethyl 3-aminocrotonate for 20 hours and the mixture is concentrated. 5.4 g of a brown oil are obtained. 5.4 g of the compound from Example 2a are dissolved in 60 ml of ethanol, 1.5 g of powdered potassium hydroxide are added and the mixture is heated under reflux for 1 hour. It is cooled, rendered neutral with 1 N hydrochloric acid and concentrated. The evaporation residue is taken up in methylene chloride, washed with water, dried and concentrated. After crystallization with ethyl acetate, the product is filtered off with suction and washed with ethyl acetate. 1.1 g of a colourless compound of melting point 218°–219° C. are obtained.

The compounds listed in Tables 1, 3, 5, 6 and 7 are prepared analogously to the instructions of Example 1:

The compounds listed in Tables 2 and 4 are prepared analogously to the instructions of Example 2:

TABLE 1

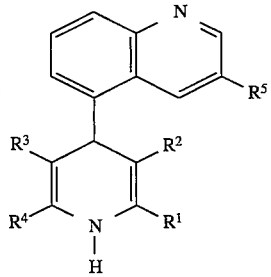

| Example No. | $R^1$ | $R^2$ | $R^3$ | $R^4$ | $R^5$ | Melting point °C. |
|---|---|---|---|---|---|---|
| 3 | $-CH_3$ | $-CO_2-(CH_2)_2-$N (pyridyl) | $-CN$ | $-CH_3$ | $-CH_2-C_6H_5$ | 205 |
| 4 | $-NH_2$ | $-CO_2CH(CH_3)_2$ | $-CN$ | $-CH_3$ | $-CH_2-C_6H_5$ | 134–136 |
| 5 | $-CH_3$ | $-CO_2CH_3$ | $-CN$ | $-CH_3$ | $-CH_2-C_6H_5$ | 174 |
| 6 | $-CH_3$ | $-CO_2(CH_2)_2CH_3$ | $-CN$ | $-CH_3$ | $-CH_2-C_6H_5$ | 116 |
| 7 | $-NH_2$ | $-CO_2C_2H_5$ | $-CN$ | $-CH_3$ | $-CH_2-C_6H_5$ | 165 |
| 8 | $-CH_3$ | $-CO_2C_2H_5$ | $-CN$ | $-CH_3$ | $-CH_2-C_6H_5$ | 193 |
| 9 | $-CH_3$ | $-CO_2CH(CH_3)_2$ | $-CN$ | $-CH_3$ | $-C(CH_3)_3$ | foam |
| 10 | $-NH_2$ | $-CO_2CH(CH_3)_2$ | $-CN$ | $-CH_3$ | $-O-C_6H_5$ | 188–189 |
| 11 | $-NH_2$ | $-CO_2(CH_2)_2CH_3$ | $-CN$ | $-CH_3$ | $-O-C_6H_5$ | 221 |
| 12 | $-CH_3$ | $-CO_2CH(CH_3)_2$ | $-CN$ | $-CH_3$ | $-O-C_6H_5$ | foam |
| 13 | $-NH_2$ | $-CO_2CH_3$ | $-CN$ | $-CH_3$ | $-O-C_6H_5$ | 242 |
| 14 | $-NH_2$ | $-CO_2CH(CH_3)_2$ | $-CN$ | $-CH_3$ | $-O-C_6H_4-p-Cl$ | 143–144 |
| 15 | $-CH_3$ | $-CO_2C_2H_5$ | $-CN$ | $-CH_3$ | $-O-C_6H_4-p-Cl$ | 196 |
| 16 | $-CH_3$ | $-CO_2CH(CH_3)_2$ | $-CN$ | $-CH_3$ | $-O-C_6H_4-p-Cl$ | 186 |
| 17 | $-NH_2$ | $-CO_2-(CH_2)_2-OCH_3$ | $-NO_2$ | $-CH_3$ | $-O-C_6H_5$ | 213 |
| 18 | $-NH_2$ | $-CO_2-CH(CH_3)_2$ | $-NO_2$ | $-CH_3$ | $-O-C_6H_5$ | 172 |
| 19 | $-CH_3$ | $-CO_2CH_3$ | $-NO_2$ | $-CH_3$ | $-c-C_6H_{11}$ | 270 (decomposition) |
| 20 | $-CH_3$ | $-CO_2CH_3$ | $-CN$ | $-CH_3$ | $-c-C_6H_{11}$ | 263–265 |
| 21 | $-CH_3$ | $-CO_2CH(CH_3)_2$ | $-CN$ | $-CH_3$ | $-c-C_6H_{11}$ | 191 |

TABLE 1-continued

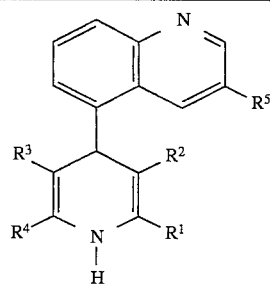

| Example No. | R¹ | R² | R³ | R⁴ | R⁵ | Melting point °C. |
|---|---|---|---|---|---|---|
| 22 | —CH₃ | —CO₂C₂H₅ | —CN | —CH₃ | —CH(CH₃)₂ | 120–121 |
| 23 | —CH₃ | —CO₂CH₃ | —CN | —CH₃ | —CH(CH₃)₂ | 164–166 |
| 24 | —CH₃ | —CO₂C₂H₅ | —CN | —CH₃ | -c-C₆H₁₁ | 228 |
| 25 | —NH₂ | —CO₂CH(CH₃)₂ | —CN | —CH₃ | -c-C₆H₁₁ | 212 (decomposition) |
| 26 | —NH₂ | —CO₂CH₃ | —CN | —CH₃ | —CH(CH₃)₂ | 160–161 |
| 27 | —NH₂ | —CO₂C₂H₅ | —CN | —CH₃ | -c-C₆H₁₁ | 170 |
| 28 | —NH₂ | —CO₂CH₃ | —CN | —CH₃ | -c-C₆H₁₁ | 238 |
| 29 | —NH₂ | —CO₂C₂H₅ | —CN | —CH₃ | —CH(CH₃)₂ | 141–142 |
| 30 | —NH₂ | —CO₂CH(CH₃)₂ | —CN | —CH₃ | —CH(CH₃)₂ | 223–224 |
| 31 | —CH₃ | —CO₂CH(CH₃)₂ | —CN | —CH₃ | —CH(CH₃)₂ | 172–173 |
| 32 | —CH₃ | —CO₂CH₃ | —CN | —CH₃ | —S—C₆H₅ | 207–208 |
| 33 | —CH₃ | —CO₂CH(CH₃)₂ | —CN | —CH₃ | —S—C₆H₅ | 160–162 |
| 34 | —CH₃ | —CO₂CH₃ | —CN | —CH₃ | —C(CH₃)₃ | 149–150 |
| 35 | —NH₂ | —CO₂CH(CH₃)₂ | —CN | —CH₃ | —C(CH₃)₃ | 217–218 |
| 36 | —CH₃ | —CO₂C₂H₄—CN | —CN | —CH₃ | —C(CH₃)₃ | 184–185 |

TABLE 2

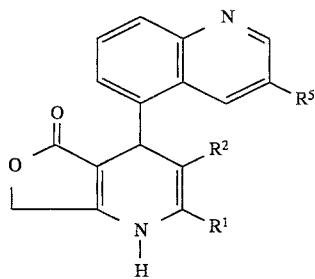

| Example No. | R¹ | R² | R⁵ | Melting point °C. |
|---|---|---|---|---|
| 37 | —CH₃ | —CO₂CH(CH₃)₂ | —O—C₆H₅ | 198 |
| 38 | —NH₂ | —CO₂C₂H₅ | -c-C₆H₁₁ | 192 |
| 39 | —CH₃ | —CO₂CH₃ | -c-C₆H₁₁ | from 262 (decomposition) |
| 40 | —CH₃ | —CO₂CH(CH₃)₂ | -c-C₆H₁₁ | from 150 |
| 41 | —NH₂ | —CO₂CH(CH₃)₂ | -c-C₆H₁₁ | from 192 |
| 42 | —CH₃ | —CO₂CH₃ | —S—C₆H₅ | 278–279 |
| 43 | —CH₃ | —CO₂CH₃ | —CH(CH₃)₂ | 158–160 |
| 44 | —NH₂ | —CO₂CH₃ | —CH(CH₃)₂ | 170–171 |
| 45 | —CH₃ | —CO₂C₂H₅ | —CH₂—C₆H₅ | 240 |
| 46 | —CH₃ | —CO—CH₃ | —CH₂—C₆H₅ | 271 |
| 47 | —CH₃ | —COO(CH₂)₂—OCH₃ | —C(CH₃)₂ | 195–196 |

TABLE 3

[Structure: 1,4-dihydropyridine with quinolinyl substituent at 4-position, R¹, R² at 2,3-positions, R³, R⁴ at 5,6-positions, R⁵ on quinoline]

| Example No. | R¹ | R² | R³ | R⁴ | R⁵ | Melting point °C. |
|---|---|---|---|---|---|---|
| 48 | —NH₂ | —COO—CH(CH₃)₂ | —CN | —CH₃ | —CH₂—(cyclohexyl) | 144 |
| 49 | —CH₃ | —COOCH₃ | —CN | —CH₃ | —CH₂—(cyclohexyl) | 128–29 |
| 50 | —CH₃ | —COO—(CH₂)₂—(2-pyridyl) | —CN | —CH₃ | —C(CH₃)₃ | 188–89 |
| 51 | —CH₃ | —COO—(CH₂)₂—N(CH₃)—CH₂—(phenyl) | —CN | —CH₃ | (cyclohexyl) | 170–71 |
| 52 | —C₂H₅ | —COO—CH(CH₃)₂ | —CN | —CH₃ | (cyclohexyl) | 215–16 |
| 53 | —NH₂ | —COO—CH₂—(cyclopropyl) | —CN | —CH₃ | (cyclohexyl) | (−)-enantiomer |
| 54 | —CF₃ | —COOCH(CH₃)₂ | —CN | —CH₃ | (cyclohexyl) | 218 |
| 55 | —CH₃ | —COO(CH₂)₂—O—CH₃ | —CN | —CH₃ | (cyclohexyl) | 219 |
| 56 | —CH₃ | —COOCH(CH₃)₂ | —CN | —CH₃ | —CH₂—(cyclohexyl) | 182 |
| 57 | —NH₂ | —COO—(CH₂)₂—CH₃ | —CN | —CH₃ | —CH₂—(cyclohexyl) | 191 |
| 58 | —CF₃ | —COOC₂H₅ | —CN | —CH₃ | (cyclohexyl) | 230 |
| 59 | —NH₂ | —COOCH₃ | —CN | —CH₃ | —C(CH₃)₃ | 174 |

TABLE 3-continued

[Structure: quinoline attached at position 5 to C4 of a 1,4-dihydropyridine; R⁵ on quinoline position 3; R¹, R², R³, R⁴ on dihydropyridine ring; NH at position 1]

| Example No. | R¹ | R² | R³ | R⁴ | R⁵ | Melting point °C. |
|---|---|---|---|---|---|---|
| 60 | −NH₂ | −COOCH₂−CH₂−OCH₃ | −CN | −CH₃ | cyclohexyl | 217 |
| 61 | −NH₂ | −COO−CH₂−CH₂−CH₃ | −CN | −CH₃ | cyclohexyl | 185 |
| 62 | −NH₂ | −COO−CH(CH₃)−COOCH₃ | −CN | −CH₃ | cyclohexyl | 191 |
| 63 | −CH₃ | −COO(CH₂)₂−CH₃ | −CN | −CH₃ | −CH₂−cyclohexyl | 209 |
| 64 | −CH₃ | −CO−NH−cyclopropyl | −CN | −CH₃ | cyclohexyl | 184 |
| 65 | −CH₃ | −COO−CH₂−CH₂−N(CH₃)−CH₂−phenyl | −CN | −CH₃ | −C(CH₃)₃ | 172 |
| 66 | −C₂H₅ | −COOC₂H₅ | −CN | −CH₃ | cyclohexyl | 220 |
| 67 | −CH₃ | −COO−CH₂−CH₂−(2-pyridyl) | −CN | −CH₃ | cyclohexyl | 228 |
| 68 | −NH₂ | −COO−CH₂−CH₂−cyclopropyl | −CN | −CH₃ | cyclohexyl | (−)-enantiomer |
| 69 | NH₂ | −COO−CH₂−CH₂OCH₃ | CN | −CH₃ | −CH₂−cyclohexyl | 174 |
| 70 | CH₃ | −COOC₂H₅ | CN | CH₃ | −CH₂−cyclohexyl | 208 |

TABLE 3-continued

[Structure: 1,4-dihydropyridine substituted with quinolin-5-yl group at position 4, with R¹, R², R³, R⁴ substituents on the pyridine ring and R⁵ on the quinoline]

| Example No. | R¹ | R² | R³ | R⁴ | R⁵ | Melting point °C. |
|---|---|---|---|---|---|---|
| 71 | NH₂ | COO—CH₂—CH₂—OCH₃ | —CN | —CH₃ | cyclohexyl | (−)-enantiomer |
| 72 | CH₃ | —COO—CH₂—CH₂—CN | —CN | —CH₃ | —CH₂-cyclohexyl | 226 |
| 73 | CH₃ | —COO—CH₂—CH₂—N(CH₃)—CH₂—Ph | —CN | —CH₃ | —CH₂-cyclohexyl | 154 |
| 74 | CH₃ | —COO—CH₂-cyclohexyl | —CN | —CH₃ | cyclohexyl | 264–68 |
| 75 | CH₃ | —COO—CH₂—CH₂—CN | —CN | —CH₃ | cyclohexyl | 186 |
| 76 | CH₃ | —COO—CH₂—CH₂—O—COCH₃ | —CN | —CH₃ | cyclohexyl | 225 |
| 77 | CH₃ | —COO-(N-methylpiperidin-4-yl) | —CN | CH₃ | cyclohexyl | 218 |
| 78 | CH₃ | —COO—CH₂—CH(CH₃)₂ | —CN | —CH₃ | cyclohexyl | 227–28 |
| 79 | CH₃ | —COO—(CH₂)₃—CH₃ | —CN | —CH₃ | cyclohexyl | 240–42 |
| 80 | CH₃ | —CO—NH-cyclopropyl | —CN | —CH₃ | —CH₂-cyclohexyl | 197–98 |
| 81 | CH₃ | —CO—NH—CH₃ | —CN | CH₃ | —CH₂-cyclohexyl | 173–74 |

TABLE 3-continued

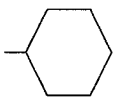

| Example No. | $R^1$ | $R^2$ | $R^3$ | $R^4$ | $R^5$ | Melting point °C. |
|---|---|---|---|---|---|---|
| 82 | $CH_3$ | —CO—NH—$CH_3$ | —CN | —$CH_3$ | cyclohexyl | 209 |
| 83 | $CH_3$ | —CO—NH—$(CH_2)_2$—$CH_3$ | —CN | —$CH_3$ | —$CH_2$-cyclohexyl | 163 |
| 84 | $CH_3$ | —CO—NH—$CH_2$—$CH_3$ | —CN | —$CH_3$ | cyclohexyl | 147 |
| 85 | $CH_3$ | —CO—NH—$(CH_2)_2$—$CH_3$ | —CN | $CH_3$ | cyclohexyl | 158–60 |
| 86 | $CH_3$ | —COOCH$_3$ | —$NO_2$ | —$CH_3$ | —$CH_2$-cyclohexyl | 251–52 |
| 87 | $CH_3$ | —CO—NH—cyclopropyl | —$NO_2$ | —$CH_3$ | —$CH_2$-cyclohexyl | 263–64 |
| 88 | $CH_3$ | —CO—NH—cyclopropyl | —CN | —$CH_3$ | cyclohexyl | (−)-enantiomer 192–93 |

TABLE 4

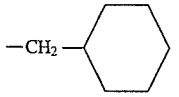

| Example No. | $R^1$ | $R^2$ | $R^5$ | Melting Point °C. |
|---|---|---|---|---|
| 89 | $CH_3$ | —COOCH$_3$ | —$CH_2$-cyclohexyl | 215–16 |

TABLE 4-continued
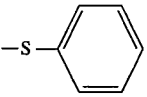
| Example No. | R¹ | R² | R⁵ | Melting Point °C. |
|---|---|---|---|---|
| 90 | NH₂ | —COOCH—(CH₃)₂ | 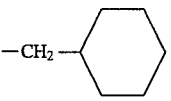 | 258 |
| 91 | CH₃ | —COOCH—(CH₃)₂ | 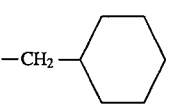 | 252 |
| 92 | NH₂ | —COOCH—(CH₃)₂ | 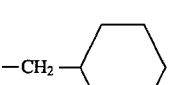 | 228 |
| 93 | NH₂ | —COOC₂H₅ |  | 166 |
| 94 | CH₃ | —CO—NH—◁ | 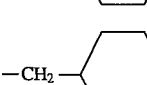 | 158–60 |
| 95 | CH₃ | —CO—NH—CH₃ | 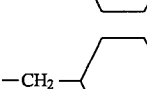 | 208–10 |
| 96 | —CH₃ | —CO—NH—CH₃ | 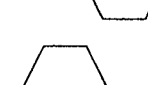 | 263 |
| 97 | —CH₃ | —CO—NH—◁ |  | 190 |
| 98 | —CH₃ | —CO₂—(CH₂)₂— | 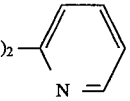 | 218 |
| 99 | —CH₃ | —CO₂—CH₂—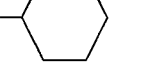 | 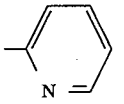 | 235 |

TABLE 5

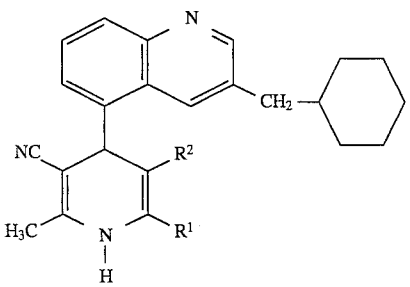

| Example No. | $R^1$ | $R^2$ | Melting Point °C. |
|---|---|---|---|
| 100 | $-CH_3$ | $-CO_2-(CH_2)-O-CO-CH_3$ | 138–40 |
| 101 | $-CH_3$ | $-CO_2-(CH_2)_2-O-CH_3$ | 160 |
| 102 | $-CH_3$ | $CO_2-CH_2-\text{cyclohexyl}$ | 105 |
| 103 | $-CH_3$ | $CO_2-(CH_2)_2-\text{2-pyridyl}$ | 191 |
| 104 | $-CH_3$ | $-CO-NH-C_2H_5$ | 167–169 |
| 105 | $-NH_2$ | $-CO_2CH_3$ | 156 |

TABLE 6

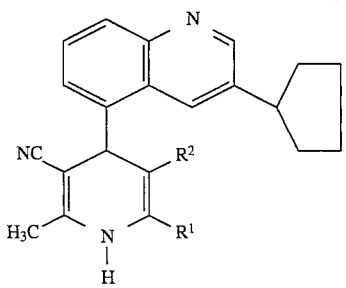

| Example No. | $R^1$ | $R^2$ | Melting Point °C. |
|---|---|---|---|
| 106 | $-CH_3$ | $-CO-NH-\text{cyclopropyl}$ | 215–217 |
| 107 | $-CH_3$ | $-CO_2-CH(CH_3)_2$ | 203–204 |
| 108 | $-CH_3$ | $-CO_2-C_2H_5$ | 148–150 |
| 109 | $-NH_2$ | $-CO_2-CH(CH_3)_2$ | 221–223 |
| 110 | $-NH_2$ | $-CO_2-C_2H_5$ | 148–149 |

TABLE 7

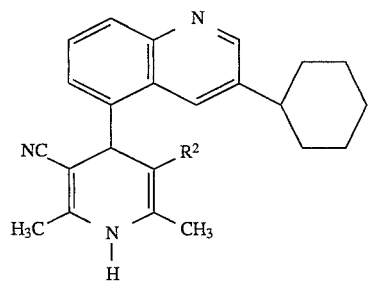

| Example No. | $R^2$ | $R^3$ | $R^4$ | Melting Point °C. |
|---|---|---|---|---|
| 111 | $-CO-NH-\text{cyclopropyl}$ | $-NO_2$ | $-CH_3$ | 184 |
| 112 | $-CO-NH-\text{cyclopropyl}$ | $-CN$ | H | 198–200 |
| 113 | $-CO-NH-\text{cyclopropyl}$ | $-CN$ | $-CH_3$ | 185–186 |
| 114 | $-CO_2CH(CH_3)_2$ | $-CN$ | $-CH_3$ | 148–150 |
| 115 | $-CO_2C_2H_5$ | $-CN$ | $-CH_3$ | 160–161 |
| 116 | $-CO_2CH_3$ | $-CN$ | $-CH_3$ | 158–160 |

TABLE 7-continued

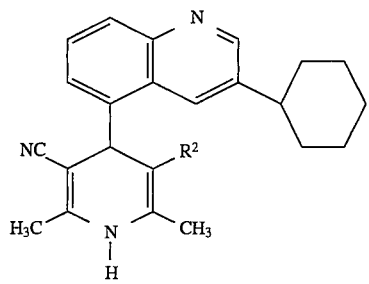

| Example No. | $R^2$ | $R^3$ | $R^4$ | Melting Point °C. |
|---|---|---|---|---|
| 117 | 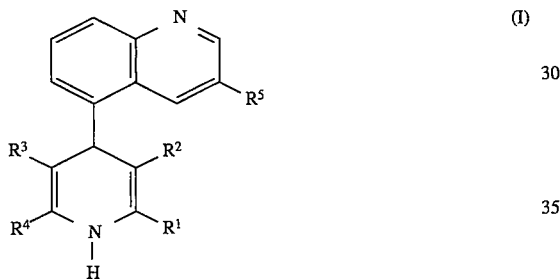 | —CN | —CH$_3$ | 250–254 R-Enantiomer [a]$_{589}^{20}$ = 370.79 (C = 0.635 Dimethylformamide) |

We claim:

1. A 3-quinolyl-substituted dihydropyridine of the formula (I)

in which $R^1$ and $R^4$ are identical or different and represent hydrogen, amino, trifluoromethyl or $C_1$-$C_4$-alkyl, $R^2$ represents a group of the formula —CO—NR$^{11}$—R$^{12}$ or —CO—A—R$^{13}$, wherein $R^{11}$ and $R^{12}$ are identical or different and denote hydrogen or a saturated or unsaturated, straight-chain, branched or cyclic hydrocarbon radical having up to 6 carbon atoms, A denotes a direct bond or an oxygen atom, $R^{13}$ denotes hydrogen or a cyclic, straight-chain or branched, saturated or unsaturated hydrocarbon radical having up to 8 carbon atoms, which is optionally interrupted by oxygen or sulphur or by —O—CO—, —CO—O— or —NR$^{16}$, wherein $R^{16}$ denotes hydrogen or methyl, and the hydrocarbon radical is optionally substituted by cyclopropyl, cyclobutyl, cyclopentyl, cyclohexyl, fluorine, chlorine, nitro, cyano, hydroxyl, —O—NO$_2$ or by phenyl, phenoxy, phenylthio or pyridyl, which can in turn be substituted by fluorine, chlorine, methyl, methoxy, methylthio, trifluoromethyl or trifluoromethoxy, or the hydrogen radical is optionally substituted by at one group of the formula CO$_2$R$^{17}$, —NH—SO$_2$X or —NR$^{20}$R$^{21}$, wherein $R^{17}$ denotes hydrogen, methyl or ethyl, $R^{20}$ and $R^{21}$ are identical or different and denote hydrogen or a straight-chain, branched or cyclic, saturated or unsaturated hydrocarbon radical having up to 5 carbon atoms, which is optionally substituted by phenyl, which in turn can be substituted by fluorine, chlorine, methyl or methoxy, or $R^{20}$ and $R^{21}$, together and including the nitrogen atom, form a piperidine or piperazine ring, which can optionally be substituted by methyl, ethyl, phenyl or benzyl, X denotes phenyl, which is optionally substituted by methyl, $R^3$ represents cyano, nitro or formyl, $R^5$ represents cycloalkyl $C_3$-$C_6$ or a straight chain or branched, saturated or unsaturated hydrocarbon radical having up to 6 carbon atoms which is optionally substituted by cyclopropyl, cyclobutyl, cyclopentyl, cyclohexyl fluorine, chlorine, cyano or hydroxyl or by phenyl, phenyloxy or phenylthio, it being possible for the cyclic radicals in turn to be substituted by fluorine, chlorine, methyl, meethoxy, trifluoromethyl or trifluoromethoxy or by a group of the formula —NR$^{24}$R$^{25}$, wherein $R^{24}$ and $R^{25}$ denote hydrogen, phenyl, benzyl or straight-chain or branched alkyl having up to 4 carbon atoms, or $R^5$ represents a group of the formula D—R$^{35}$, wherein D denotes an oxygen or sulphur atom, and $R^{35}$ denotes phenyl, which is optionally substituted by fluorine, chlorine, methyl, methoxy, methylthio, trifluoromethyl or amino or by $C_1$-$C_2$-mono- or-dialkylamino, or a pharmaceutically acceptable salt thereof.

2. A compound or salt according to claim 1, in which $R^1$ and $R^4$ are identical or different and represent hydrogen, alkyl having up to 4 carbon atoms, or amino, $R^3$ represents cyano or nitro, and $R^5$ represents a hydrocarbon radical having up to 10 carbon atoms, or $R^{13}$ and $R^4$ together form a radical of the formula

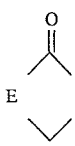

wherein

E denotes an oxygen or sulphur atom.

3. A compound or salt according to claim 1, in which $R^1$ and $R^2$ are $C_1$–$C_4$ alkyl, $R^3$ is CN or $NO_2$, $R^5$ is $C_1$–$C_3$-alkyl phenyl, cyclohexyl, $C_1$–$C_3$ alkyl cyclohexyl, phenoxythiophenoxy or $C_1$–$C_6$ straight or branched alkyl.

4. A compound according to claim 1, of the formula

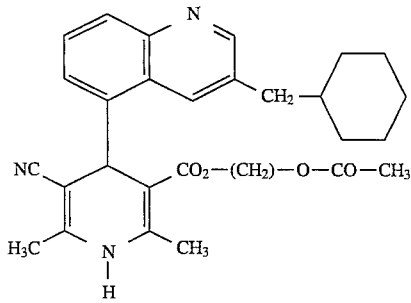

or a salt thereof.

5. A compound according to claim 1, of the formula

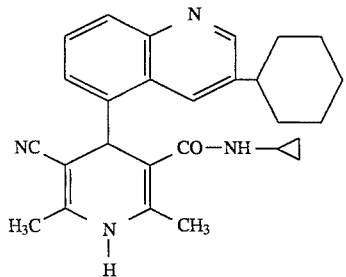

6. A cardiovascular active composition comprising a cardiovascularly effective amount of a compound or salt according to claim 1 and a physiologically acceptable diluent.

7. A method of treating a cardiovascular disorder in a patient in need thereof which comprises administering to such patient a cardiovascularly effective amount of a compound or salt according to claim 1.

8. The method according to claim 1, wherein such compound is

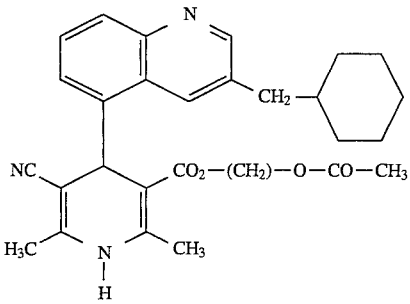

or

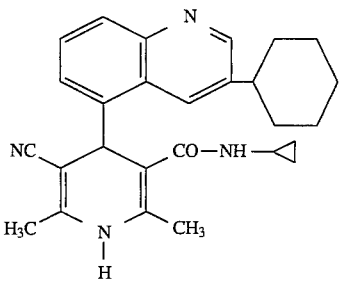

or a salt thereof.

* * * * *

UNITED STATES PATENT AND TRADEMARK OFFICE
CERTIFICATE OF CORRECTION

PATENT NO. : 5,504,210
DATED : April 2, 1996
INVENTOR(S) : Stoltefuss, et al.

It is certified that error appears in the above-indentified patent and that said Letters Patent is hereby corrected as shown below:

Col. 41, line 1   Delete " $R^{13}$ " and substitute -- $R^3$ --

Signed and Sealed this

Tenth Day of September, 1996

Attest:

BRUCE LEHMAN

*Attesting Officer*   Commissioner of Patents and Trademarks